ent Number: 4,965,371
Date of Patent: Oct. 23, 1990

United States Patent [19]
Minaskanian et al.

[54] SELECTIVE CYCLIZATION PROCESS

[75] Inventors: Gevork Minaskanian, Irvine; James V. Peck, Costa Mesa, both of Calif.

[73] Assignee: Whitby Research, Inc., Irvine, Calif.

[21] Appl. No.: 357,027

[22] Filed: May 25, 1989

Related U.S. Application Data

[62] Division of Ser. No. 847,464, Apr. 3, 1986, Pat. No. 4,870,170.

[51] Int. Cl.$^5$ .......................................... C07D 205/08
[52] U.S. Cl. .................... 548/952; 546/293; 548/533; 540/536
[58] Field of Search ...................... 540/538; 546/293; 548/533, 952

[56] References Cited
FOREIGN PATENT DOCUMENTS 0910056  4/1954  Fed. Rep. of Germany ...... 540/538

*Primary Examiner*—David B. Springer
*Attorney, Agent, or Firm*—Robert J. Baran

[57] ABSTRACT

This invention provides a process for preparing lactams, by selectively reacting a novel 1-hydrocarbylamino (or heteroatom-substituted hydrocarbylamino); 1,1-dicarboxylic acid, alkylesters; 1-hydrocarbyl (or heteroatom-substituted hydrocarbyl) carboxylic acid, alkyl ester methane, as the salt of an acid having a pKa of 0 or more, in the absence or presence of a base, whereby novel lactams wherein one or both hydrocarbyl moieties are incorporated into the lactam ring are obtained. That is, the acid moiety of said novel salt promotes the reaction whereby both hydrocarbyl moieties are incorporated into the ring, while the presence of a base, in an amount substantially equivalent to said acid promotes the reaction whereby only one hydrocarbyl is incorporated into the ring.

8 Claims, No Drawings

SELECTIVE CYCLIZATION PROCESS

This is a divisional of co-pending application Ser. No. 06/847,464 filed on Apr. 3, 1986 now U S. Pat. No. 4,870,170

BACKGROUND OF THE INVENTION

1. Field of the Invention

This invention relates to a process for preparing lactams. In particular, the present invention provides a process for selectively reacting a novel 1-hydrocarbylamino (or heteroatom-substituted hydrocarbylamino); 1,1-dicarboxylic acid, alkylesters; 1-hydrocarbyl (or heteroatom-substituted hydrocarbyl) carboxylic acid, alkyl ester methane, as the salt of an acid having a pKa of 0 or more, to provide novel lactams wherein one or both hydrocarbyl moieties are incorporated into the lactam ring. Preferably, The selectivity of the reaction is controlled by either cyclizing the novel salts, in the absence of a base, or cyclizing said novel salts, in the presence of an amount of base substantially equivalent to said acid. That is, the acid moiety of said novel salt promotes the reaction whereby both hydrocarbyl moieties are incorporated into the ring, while the presence of a base promotes the reaction whereby only one hydrocarbyl is incorporated into the ring. Therefore, reaction at neutral or slightly basic conditions provides improved selectivity to lactams having a smaller ring size, while the acid-catalyzed reaction increases the selectivity to lactams having a larger ring size.

2. Description of the Art

Lactams are cyclic amides having many uses as intermediates for the preparation of polymers, medicinals, etc. In particular, in medicinal uses, certain lactams have been found to enhance the transdermal penetration of various physiologically-active compounds into the tissues and blood stream of an animal, e.g. a human. See, for example, U.S. Pat. Nos. 3,989,816; 4,316,893; 4,310,525; 4,422,970; and 4,405,616; wherein lactams, in particular, having 1-n-alkyl azacycloalkan-2-ones, having a ring size of from 5 to 9 members are shown to enhance the transdermal penetration of physiologically-active materials. It has been found that both the size of the ring and the length of the n-alkyl group affects the transdermal penetration-enhancing properties of the 1-n-alkylazacycloalkan-2-ones disclosed in these patents. Thus, it would be desirable to have a process for selectively varying both the ring size and the length of the n-alkyl group as well as preparing novel substituted lactams for penetration enhancement. Lactams are also useful in the preparation of nylon 6-type polymers wherein the properties thereof may be systematically modified through the regulation of the nature and position of the lactam substituent. See, for example, C. G. Overberger et al., Journal of Polymer Science, Vol. 10, 2265–2289 (1972).

SUMMARY OF THE INVENTION

It has unexpectedly been found that a novel 1-hydrocarbyl-amino (or heteroatom-substituted hydrocarbylamino); 1,1-dicarboxylic acid, alkyl esters; 1-hydrocarbyl (or heteroatom-substituted hydrocarbyl) carboxylic acid, alkyl ester methane, as the salt of an acid having a pKa of 0 or more, may be selectively cyclized into a lactam, having either one or both of the hydrocarbyl moieties incorporated into the ring, by first neutralizing said acid with a substantially equivalent amount of base and then Carrying out said cyclization process or cyclizing the acid salt without neutralization, respectively.

DESCRIPTION OF THE INVENTION

The present invention provides a process for converting a first compound represented by the general formula:

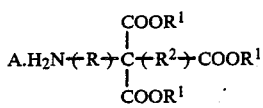

selectively into a second compound represented by the general formula:

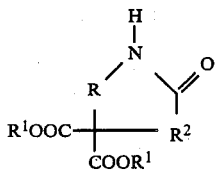

or into a second compound represented by the general formula:

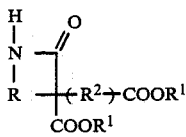

by cyclizing said first compound in the absence of a base or by neutralizing said compound with an amount of base substantially equivalent to A (A represents a weak acid, i.e. an acid having a pKa of 0 or more) and then cyclizing said first compound. Thus, either the hydrocarbyl moiety represented by R or both R and the hydrocarbyl moiety represented by $R^2$ (with the exception noted below) may be incorporated, selectively, into the resulting lactam ring by carrying out the cyclization in the absence or presence of a base.

This reaction is general in nature, provided the first compound has the structure represented by the above general formula, wherein R and $R^2$ each represent a divalent hydrocarbyl radical or a hydrocarbyl radical substituted with one or more hetero atoms selected from the group consisting of oxygen, nitrogen, sulfur, phosphorus and halogen atoms; and $R^1$ is an alkyl radical having from one to eight carbon atoms. Preferably, R and $R^2$ are selected from the group consisting of alkyl, alkenyl and heteroatom-substituted alkyl or alkenyl radicals. More preferably, R is selected from radicals represented by the general formula

wherein $R_3$ is selected from the group consisting of hydrogen, alkyl radicals having from one to six carbon atoms and phenyl and x is an integer of from 1 to 5, and $R^2$ is preferably selected from radicals represented by the general formula

wherein $R^4$ is selected from the group consisting of hydrogen, alkyl radicals having from one to six carbon atoms and phenyl and y is an integer of from 2 to 5.

It has been found that when $R^2$ represents a divalent hydrocarbon radical having more than two carbon atoms between the carboxy carbon atom and the methane carbon atom then incorporation of $R^2$ into the lactam ring does not occur even when the cyclization is carried out in the absence of a base. Therefore, for the preparation of amides wherein $R^2$ is incorporated into the lactam ring $R^2$ is selected from radicals represented by $-CR^4{}_{2y}$ above wherein y is 1 or 2.

For the purpose of selectivity to a larger or smaller ring size, even more preferably, $R^3$ and $R^4$ are hydrogen radicals, x is 2 and y is 1 or 2.

Most preferably, $R^1$ is ethyl, and y is 1.

A represents a weak acid, i.e. an acid having a pKa of 0 or more; preferably 2 or more. Suitable acids include carboxylic acids having from one to ten, more preferably from one to six carbon atoms, e.g. acetic acid and propionic acid. Halogenated carboxylic acids, e.g. fluorinated and chlorinated carboxylic acids, such as trichloroacetic acid and trifluoroacetic acid are also suitable.

Thus, 1-ethylamino, 1,1-dicarboxylic acid, ethylester,1-methylcarboxylic acid, ethyl ester methane and 1-ethylamino, 1,1-dicarboxylic acid, ethyl ester, 1-ethylcarboxylic acid, ethyl ester methane may be selectively converted into a 6-membered lactam or a 5-membered lactam and a 7-membered lactam or a 5-membered lactam, respectively.

In particular, the 7-membered lactam resulting from the cyclization of 1-ethylamino, 1,1-dicarboxylic acid, ethyl ester, 1-ethyl carboxylic acid, ethyl ester methane, is useful as an intermediate for penetration-enhancing agents of varying hydrophilicity (e.g. carboxylic acid-substituted alkyl lactams) and nylon 6-type polymers as well as medicinal agents.

The 6-membered lactam resulting from the cyclization of 1-ethylamino, 1,1-dicarboxylic acid, ethyl ester, 1-methyl carboxylic acid, ethyl ester methane is useful as an intermediate for penetration-enhancing agents of varying hydrophilicity (e.g. carboxylic acid-substituted alkyl lactams) and nylon 6-type polymers as well as medicinal agents. (Moreover, as discussed below, this representative first compound may be cyclized to the 6-membered lactam at 97 percent selectivity.)

The base may be selected from the group consisting of Group I and II metal oxides, hydroxides and carbonates or any other compound or salt which provides a pH greater than 7 when contacted with the above-defined first compound. For example, sodium hydroxide, potassium hydroxide, sodium oxide, potassium oxide, calcium oxide, calcium hydroxide, calcium carbonate, are suitable bases for the process of the present invention.

The cyclization process is varied in accordance with the desire to obtain lactams having one or both hydrocarbyl groups, represented by R and $R^2$, above, incorporated into the ring. To obtain the lactams having a larger ring size, i.e. having both R and $R^2$ incorporated in the ring, the cyclization is effected without neutralization of the acid moiety A.

This cyclization reaction is preferably carried out in an inert solvent for the first compound, e.9. a chlorinated organic solvent, such as chloroform, methylene chloride, etc., an ether, e.g. diethyl ether, tetrahydrofuran, etc.

Preferably, a chlorinated organic solvent is used to dissolve the first compound, e.g. chloroform or methylene chloride.

To obtain lactams wherein only R is incorporated in the ring, A should be neutralized with a substantially equivalent amount of a base prior to cyclization. (For the purposes of this invention, an equivalent amount of base may vary from 0.8 to 1.2 per equivalent of A. Preferably, the amount of base varies from 0.9 to 1.1 per equivalent of A.)

Thus, the first compound may be mixed with an aqueous solution containing an amount of base substantially equivalent to A and the resulting lactam subsequently extracted with a solvent, e.g. one of the organic solvents described above. (It should be noted that the identity of A is not limited to acids having a pKa of 0 or more, when cyclization, in the presence of a substantially equivalent amount of base, is carried out to obtain lactams wherein only R is incorporated into the ring. That is, salts of the first compound and an acid having a pKa of less than 0, e.g. hydrochloric acid, may be neutralized with a substantially equivalent amount of base and then cyclized to a lactam wherein R (only) is incorporated into the ring.)

Alternatively, the first compound may be mixed with water and the resulting mixture stirred in the presence of water-immiscible solvent for the lactam. To this two phase mixture, aqueous base may be slowly added whereby the acid is neutralized and dissolves in the aqueous phase and the resulting lactam dissolves in the water-immiscible solvent. Again, the water-immiscible solvent may be selected from the organic solvents described above, with the chlorinated solvents such as chloroform and methylene chloride being preferred.

The present process may be carried out at a temperature of from 0° to 150° C.; preferably from 0° to 50° C., and a pressure of from 1 to 10 atmospheres; preferably from 1 to 5 atmospheres. For convenience, ambient conditions may be used. Preferably, for increased selectivity, the cyclization in the absence of base is carried out at from 25° to 50° C., while cyclization in the presence of a base is carried out at about 0° C.

It has been found that the length of the $R^2$ moiety affects selectivity, with longer chain lengths favoring the formation of lactams wherein only R is incorporated into the ring. Moreover, when the above-defined first compound, is prepared as a salt of an acid, e.g. the acetate, it is important to immediately carry out the base-catalyzed reaction, if high selectivity to the resulting base catalyzed product is desired. For example, when the freshly-prepared acetate salt of 1-ethylamino, 1,1-dicaboxylic acid, ethyl ester, 1-methylcaboxylic acid, ethyl ester methane is immediately neutralized with sodium hydroxide, a selectivity to the 5-membered lactam of 75 percent is obtained. However, stirring the unneutralized salt overnight provides the 6-membered lactam at a selectivity of 97 percent, demonstrating that, when thermodynamically favorable, the first compound will cyclize to the second compound having the larger ring size with time.

The invention is further illustrated by the following-examples which are illustrative of various aspects of the invention, and are not intend as limiting the scope of the invention as defined by the appended claims.

EXAMPLE 1

Preparation of 1-Methyl cyano, 1,1 dicarboxylic acid, ethyl ester, 1-methyl carboxylic acid, ethyl ester methane.

A flame-dried flask was charged with a stirred suspension of 2.0 g (0.05 mol) of sodium hydride (60% dispersion in mineral oil); washed free of oil with 2×20 mL of dry pet ether) in 150 mL of dry tetrahydrofuran (THF) under nitrogen at 0° C. To the suspension, 10 g (0.05 mol) of ethyl 2-carboethoxy-3-cyano propionate was added dropwise and the mixture refluxed for 30 min. To the clear solution was added a solution of 6.1 g (0.05 mol) of ethyl chloracetate in 10 mL dry THF and refluxing was continued overnight. Water (10 mL) was added and the product extracted with 2×100 mL portions of chloroform. The organic extracts were combined, washed with water, saturated sodium chloride, dried over anhydrous magnesium sulfate, and evaporated. The product was distilled under high vacuum to give 9.0 g (60%) of a clear colorless oil: bp 114°-115° C. (0.2 mm); IR (CHCl$_3$) 2250, 1740 cm$^1$; NMR (CDCl$^3$, 60 MHz) 4.2 (6H, q), 3.15 (2H, s), 3.05 (2H, s),, 1.25 (9H, t).

EXAMPLE 2

3-(Ethoxycarbonyl)-2-oxo-3-pyrrolidineacetic acid ethyl ester

To a solution of 7.8 g (0.027 mol) of the cyanotriester from Example 1 in 75 mL of glacial acetic acid was added 300 mg of platinum (IV) oxide, and the suspension was vigorously agitated under hydrogen (60 psi) for 36 h. The mixture was filtered through celite and acetic acid was removed under reduced pressure (Ca. 0.5 mm) at 30°-35° C. To the ice-cold oily residue was added 100 mL of 1N NaOH in one portion. The mixture was quickly extracted with 3×50 mL dichloromethane and the combined organic layer was subsequently washed with saturated sodium chloride solution and dried with magnesium sulfate and solvent was removed in vacuo. GC analysis of the crude mixture (injector 300° C., detector 300° C., column 150° C., program was started after 1 min., 30° C./min to 250° C.) showed 76% of diester-lactam. Upon flash chromatography (silica, 1:1, EtOAc/pet ether), a total of 48 g (73%) of product was obtained as white solid: mp 93°-94° C., IR (CHCl$_3$) 1735, 1700 cm$^{-1}$; NMR (CDCl$_3$) 6.7 (1H, br), 4.2 (4H, q), 3.6 (1H, m), 3.4 (1H, m), 3.25 (1H, d), 2.85 (1H, m), 2.6 (1H, d), 2.2 (1H, m), 1.25 (6H, t).

Anal. Calcd. for C$_{11}$H$_{17}$NO$_5$: C, 54.31; H, 7.04; N, 5.76. Found: C, 54.34; H, 6.89; N, 5.82.

EXAMPLE 3

2-Oxo-4,4-piperidinedicarboxylic acid diethyl ester

To the oily residue from the previous experiment (containing a trace amount of acetic acid) was added 100 mL of chloroform, and the solution was stirred at room temperature for 3 days. The chloroform was removed and the residue washed with pet ether, dried over MgSO$_4$, and concentrated to give 6.5 g of white solid. GC analysis of crude product over the same conditions described previously showed 97% of diester-lactam with a retention time of 4.17 min. Product was recrystallized from EtOAc/pet ether to give 6.5 g (95%) of white crystalline solid: mp 87°-88° C.; IR (CHCl$_3$) 1730, 1670 cm$^{-1}$; NMR (CDCl$_3$) 7.5 (1H, br), 4.2 (4H, q), 3.25 (2H, dt), 2.7 (2H, s), 2.25 (2H, t), 1.25 (6H, t).

Anal. Calcd. for C$_{11}$H$_{17}$NO$_5$: C, 54.31; H, 7.04; N, 5.76. Found: C, 54.54; H, 7.19; N, 5.88.

EXAMPLE 4

Preparation of 1-Methyl cyano, 1.1 dicarboxylic acid, ethyl ester, 1-ethyl carboxylic acid, ethyl ester methane.

Alkylation of 20.0 (0.10 mol) of ethyl-2-carboethoxy-3-cyano propionate with 18.0 g (0.10 mol) of 3-bromopropionate resulted in 29.6 g of crude oil. Upon flash chromatography (silica, 25% ether/pet ether), and Kugelrohr distillation, 22.3 g (74%) of the product isolated as a clear oil: bp 130°-135° C. (0.2 mm); IR (neat) 2250, 1720 cm$^{-1}$; NMR (CDCl$_3$), 60 MHz) 4.15 (6H, m), 2.9 (2H, s), 2.35 (4H, s), 1.3 (9H, t).

Anal. Calcd. for C$_{14}$H$_{21}$NO$_6$: C, 56.18; H, 7.07; N, 4.68. Found: C, 55.83; H, 7.08; N, 4.90.

EXAMPLE 5

Hexahydro-7-oxo-4H-Azepine-4,4-dicarboxylic acid diethyl ester

A solution of 14.32 g (47.8 mmol) of the cyanotriester from Example 4 in 150 mL of glacial acetic acid was hydrogenated (60 psi) with 250 mg of platinum (IV) oxide as described previously. After workup, to the oil residue was added 200 mL of chloroform and the solution stirred for 3 days at room temperature. The solvent was removed in vacuo and the residue triturated in pet ether (3×50 mL). The solid residue was subjected to flash chromatography (silica, EtOAC) to give white solid: mp 80°-81° C.; IR (CHCl$_3$) 1725, 1665 cm$^{-1}$; NMR (CDCl$_3$, 250 MHz) 6.15 (1H, br), 4.19 (4H, q, J=7.2 Hz), 3.3 (2H, m), 2.48 (2H, m), 2.28-2.12 (4H, m), 1.24 (6H, t, J=7.2 Hz).

Anal. Calcd. for C12H$_{19}$NO$_5$ : C, 56.02; H, 7.44; N, 5.44. Found: C, 55.80; H, 7.39; N, 5.38.

EXAMPLE 6

3-(Ethoxycarbonyl)-2-ones-4-pyrrolidinebutyric acid diethyl ester

To the oily residue from previous experiment was added base and extracted as described before to give the pyrrolidinediester with a R$_f$ of 0.37 (silica,, EtOAc). After flash chromatography the product was obtained as white solid: mp 57°-58° C.; IR (CHCl$_3$) 1740-1700 cm$^{-1}$; NMR (CDCl$_3$);, 250 MHz) 6.6 (1H, br), 4.19 (2H,, q, J=7.3 Hz), 4.10 (2H, q, J=7.3 Hz), 3.43 (H, m, 3.32 (1H, m), 2.56 (1H, m), 2.45 (1H, m), 2.31 (2H, m), 2.06 (2H, m), 1.25 (3H, t, J=7.3 Hz), 1.23 (3H, t, J=7.3 Hz.)

Anal. Calcd. for C$_{12}$H$_{19}$NO$_5$: C, 56.02; H, 7.44; N, 5.44. Found: C, 55.80; H, 7.39; N, 5.38.

EXAMPLE 7

Preparation of 1-Methylcyano, 1,1 dicarboxylic acid, ethyl ester, 1-n-propyl carboxylic acid, ethyl ester methane.

Alkylation of 20 g (0.10 mol) of ethyl-2-carboethoxy-3-cyano propionate with 19.5 g (0.1 mol) of ethyl 4-bromobutyrate resulted in 38.5 g of crude oil. Upon fractional distillation, product was obtained as a clear oil: bp 150°-165° C. (0.4 mm), IR (neat) 2250, 1740 cm$^{-1}$, NMR (CDCl$_3$) 4.0 (6H, m), 2.8 (2H, s). 2.3-1.3 (6H, m), 1.2 (3H, t).

Anal. Calcd. for $C_{15}H_{23}NO_6$: C, 57.50; H, 7.40; N, 4.47. Found: C, 57.78; H, 7.27; N, 4.98.

EXAMPLE 8

3-(Ethoxycarbonyl)-2-oxo-5-pyrrolidinevaleric acid diethyl ester

A solution of 10 g (32 mmol) of the cyanotriester from Example 7 in 80 mL of glacial acetic acid was hydrogenated (60 psi) with 250 mg of platinum (IV) oxide as described previously. After workup, to the oily residue was added 200 mL of chloroform and the solution stirred for 3 days at room temperature. The solvent was removed in vacuo and the residue was subjected to flash chromatography (silica, 75% ethyl acetate/hexane) to yield 6.54 g (75%) of a white solid: mp 72°–73° C.; IR (CHCl$_3$) 1740–1700 cm$^{-1}$; NMR (CDCl$_3$, 250 MHz) 6.4 (1H, br), 4.18 (2H, q, J=7.2 Hz), 4.10 (2H, q, J=7.2 Hz), 3.45 (1H, m), 3.31 (H, m), 2.61 (1H, m), 2.33 (2H, m), 2.08 (2H, m), 1.66 (3H, m), 1.25 (3H, t, J=7.2 Hz), 1.23 (3H, t, J=7.2 Hz).

While particular embodiments of the invention have been described it will be understood of course that the invention is not limited thereto since many obvious modifications can be made and it is intended to include within this invention any such modifications as will fall within the scope of the appended claims.

What is claimed is:

1. A process for converting a first compound represented by the general formula:

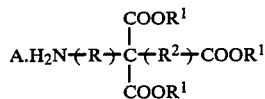

selectively into a second compound represented by the general formula:

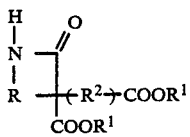

wherein R represents an alkylene or alkenylene radical containing 1 or 2 carbon atoms; R$^2$ is selected from radicals represented by the general formula:

$$-CR_2^4-y$$

wherein R$^4$ is selected from the group consisting of hydrogen, alkyl radicals and phenyl and y is an integer of from 1 or 5; R$^1$ is an alkyl radical, having from one to eight carbon atoms, and A is an acid selected from the group consisting of carboxylic acids having between 1 and 10 carbon atoms, which process comprises the step neutralizing the acid with a substantially equivalent amount of a base and cyclizing said first compound at a temperature sufficient to cause cyclization to form at most a four-membered ring lactam.

2. The process of claim 1 wherein R$^1$ is ethyl.

3. The process of claim 2 wherein y is 1.

4. The process of claim 1 wherein said second compound is reacted with said base in an aqueous solution at a temperature of from 0° C. to 25° C. and said second compound is recovered by extraction from said aqueous solution with an inert organic solvent.

5. The process of claim 4 wherein said inert organic solvent is an alkyl chloride.

6. The process of claim 1 wherein said first compound is reacted with said base by stirring an aqueous solution of said base and said first compound in the presence of chloroform at a temperature of from 0° C. to room temperature.

7. The process of claim 1 wherein said base is selected from the group consisting of Group I and II metal oxides, hydroxides and carbonates.

8. The process of claim 7 wherein said base is sodium hydroxide.

* * * * *